United States Patent [19]
Ito et al.

[11] Patent Number: 6,090,732
[45] Date of Patent: Jul. 18, 2000

[54] ZINC-DOPED TRICALCIUM PHOSPHATE CERAMIC MATERIAL

[75] Inventors: Atsuo Ito, 528-404, Matsushiro 5-chome, Tsukuba-shi, Ibaraki-ken; Noboru Ichinose, Tokyo-to; Kenji Ojima, Yokohama, all of Japan; Pierre Layrolle, Utrecht, Netherlands; Haruo Kawamura, Tsukuba, Japan

[73] Assignees: Japan as Represented by Director General of Agency of Industrial Science and Technology, Tokyo-to; Atsuo Ito, Tsukuba, both of Japan

[21] Appl. No.: 09/199,333

[22] Filed: Nov. 25, 1998

[30] Foreign Application Priority Data

Nov. 27, 1997 [JP] Japan ..................... 9-342033

[51] Int. Cl.[7] .............................. C01B 25/222; A61F 2/28
[52] U.S. Cl. ................. 501/1; 501/123; 106/35; 424/602; 424/604
[58] Field of Search .................... 501/1, 123; 106/35; 423/311; 424/602, 604

[56] References Cited

U.S. PATENT DOCUMENTS 4,376,168  3/1983  Takani et al. .
4,778,471  10/1988  Bajpai .

FOREIGN PATENT DOCUMENTS 0 372 676  6/1990  European Pat. Off. .
0 508 524  10/1992  European Pat. Off. .
0 555 807  8/1993  European Pat. Off. .
1487181  9/1977  United Kingdom .

OTHER PUBLICATIONS

P. Layrolle et al., *Phos. Res. Bull.*, 6, 63–66 (1996). no month.
E. Kreidler et al., *Inorg. Chem.*, 6(3), 524–528 (1967). no month.
A. Bigi et al., *J. Inorg. Chem.*, 66, 259–265 (1997). no month.
M. Yamaguchi et al., *Biochem. Pharm.*, 36(22), 4007–4012 (1987). no month.

*Primary Examiner*—C. Melissa Koslow
*Attorney, Agent, or Firm*—Wenderoth, Lind & Ponack, L.L.P.

[57] ABSTRACT

A tricalcium-phosphate-based prosthetic material is disclosed, which is a sintered ceramic body mainly consisting of tricalcium phosphate containing a limited amount of zinc, which is a known element having an osteogenesis-promoting effect, in the form of a solid solution. By virtue of the limited content of zinc and the form of solid solution in which zinc is contained, the inventive material exhibits an osteogenesis-promoting effect without toxicity. The ceramic body is prepared, preferably, by a process in which a tricalcium phosphate powder containing 0.015–8.00% by weight of zinc is diluted by the addition of hydroxyapatite and/or tricalcium phosphate free from zinc in such a proportion as to give a (Ca+Zn)/P molar ratio of 1.55 to 1.65 and the powder blend is shaped and subjected to sintering.

4 Claims, 9 Drawing Sheets

FIG. 3

FIG.5

ZINC-DOPED TRICALCIUM PHOSPHATE CERAMIC MATERIAL

BACKGROUND OF THE INVENTION

The present invention relates to a ceramic material based on tricalcium phosphate $Ca_3(PO_4)_2$ doped with a limited amount of zinc. More particularly, the invention relates to a ceramic body containing tricalcium phosphate doped with zinc suitable as a surgical implant for a hard-tissue of a living body.

As is known, several ceramic materials are officially approved for use as a surgical implant for hard-tissue in the living body including alumina, hydroxyapatite, tricalcium phosphate, AW-glass ceramic, carbon and the like. A ceramic material for a surgical implant has no pharmaceutical effect to promote bone formation, to inhibit bone resorption, or to promote tissue restoration. Therefore, it is necessary for a patient to be administered with some supplemental medicines in addition to the surgical implants in order to promote bone formation, to inhibit bone resorption, or to promote tissue restoration. It is desirable that a surgical implant in itself may have such pharmaceutical effects.

On the other hand, zinc is known to have the above mentioned pharmaceutical effects when taken into a living body in a limited dose although toxicity appears by a large amount of zinc dose. Accordingly, zinc-containing ceramic materials are proposed for use as a bone substitute material including those consisting of 10 to 50% by weight of ZnO, 30 to 40% by weight of CaO and 10 to 40% by weight of $P_2O_5$ and those consisting of 10 to 50% by weight of $ZnSO_4$, 30 to 40% by weight of CaO and 10 to 40% by weight of $P_2O_5$ (see U.S. Pat. No. 4,778,471) and those consisting of 7% by weight of ZnO, 25% by weight of CaO and 68% by weight of $P_2O_5$ (see U.S. Pat. No. 4,376,168). These zinc-containing ceramic materials, however, are considered not to be quite satisfactory as a bone substitute with the pharmaceutical effects because the ceramic materials contain, besides the phases of tricalcium phosphate and hydroxyapatite, several other phases having lower biocompatibility or safety to a living body. This is because they contain a relatively large amount of zinc. No animal tests undertaken with these zinc-containing ceramic materials demonstrated the above mentioned pharmaceutical effects.

Further, it is known that a ceramic body consisting of the phases of tricalcium phosphate and/or hydroxyapatite has the best biocompatibility with hard tissues. When such a ceramic body is implanted in a bone, direct connection is formed between the bone and the ceramic body without intervention of any fibrous connective tissues. Accordingly, it is desired to develop a hard-tissue substitute having both the above mentioned pharmaceutical effects and high biocompatibility. Extensive investigations have been undertaken therefore to obtain a zinc-doped ceramic material consisting of the phase of tricalcium phosphate, optionally, in combination with the phase of hydroxyapatite exhibiting high biocompatibility and capable of promoting bone formation by releasing zinc within a living body.

SUMMARY OF THE INVENTION

The present invention accordingly has an object to provide a novel zinc-containing or zinc-doped ceramic material mainly consisting of tricalcium phosphate and suitable as a ceramic material for biomedical use or, in particular, to provide surgical implant materials for hard-tissue containing or consisting of zinc-doped tricalcium phosphate to promote bone formation by releasing zinc in the living body.

Thus, the present invention provides a ceramic body consisting of tricalcium phosphate doped with zinc in an amount in the range from 0.0126 to 1.26% by weight calculated as zinc based on the weight of the ceramic material.

Further, the present invention provides a composite ceramic material doped with zinc in an amount in the range from 0.0126 to 1.26% by weight prepared by a process in which tricalcium phosphate doped with zinc in an amount in the range from 0.0150 to 8.00% by weight calculated as zinc in the form of a solid solution is admixed with hydroxyapatite and/or undoped tricalcium phosphate in such an amount that the content of zinc in the mixture is in the range from 0.0126 to 1.26% by weight and the mixture is subjected to sintering.

In addition, the present invention provides a material for surgical implant for hard-tissues which is a sintered body of a zinc-doped ceramic material as defined above.

DETAILED DESCRIPTION OF THE PREFERRED EMBODIMENTS

As is described above, the principal constituent of the inventive ceramic material is tricalcium phosphate doped with a specified amount of zinc in the form of a solid solution and the ceramic material is characterized by a specified overall amount of zinc contained therein as a dopant in the range from 0.0126 to 1.26% by weight or, preferably, from 0.06 to 0.70% by weight based on the weight of the ceramic material. The phase of zinc-doped tricalcium phosphate can optionally be combined with the phases of undoped tricalcium phosphate and/or hydroxyapatite to form a composite ceramic material, of which the overall content of zinc in the composite ceramic material is also in the range from 0.0126 to 1.26% by weight or, preferably, from 0.06 to 0.70% by weight.

The above defined zinc-doped-tricalcium-phosphate-based ceramic materials are suitable for use as a material for hard-tissue replacement, augmentation or reconstruction.

The zinc-doped-tricalcium-phosphate-based ceramic material in the form of a powder can be prepared by a conventional method known per se for the preparation of ceramic materials including the solid-phase reaction methods, liquid-phase reaction methods and mechanochemical reaction methods from the starting materials including zinc compounds or zinc ions, calcium compounds or calcium ions and phosphate compounds or phosphate ions. Among these known methods, the ceramic powder is prepared preferably by the liquid-phase reaction method in view of the good sintering behavior of the powder prepared by the method in the form of precipitates.

In conducting the liquid-phase reaction method for the preparation of the ceramic powder, solutions capable of forming tricalcium phosphate by blending are admixed with a soluble zinc compound in a calculated amount to give a desired content of the zinc dopant. The solutions are mixed together to effect co-precipitation of zinc with tricalcium phosphate. The precipitates are collected by filtration followed by drying and calcination. The thus-obtained ceramic powder is blended with a binder and shaped into a green body which is subjected to sintering at a high temperature to give a sintered body used as a material to serve as a surgical implant for a hard-tissue.

The solutions from which tricalcium phosphate can be formed by blending include a combination of a solution of a calcium alkoxide, e.g., calcium ethoxide, and a solution of phosphoric acid, a combination of a suspension of calcium hydroxide and a phosphoric acid solution, a combination of a calcium nitrate solution and an ammonium phosphate solution and a combination of a phosphoric acid solution and a calcium carbonate suspension, though not particularly limitative thereto. Zinc can be introduced into the solution to form tricalcium phosphate in the form of a compound including zinc carboxylates such as zinc acetate, zinc nitrate, zinc phosphate, zinc carbonate, zinc lactate and the like. The amount of the zinc compound should be selected according to a calculation that the tricalcium phosphate-based ceramic material prepared from the mixture may contain from 0.0126 to 1.26% by weight or, preferably, from 0.06 to 0.70% by weight of zinc. The precipitates of tricalcium phosphate containing zinc are collected by filtration, dried at 40 to 150° C. or, preferably, at 60 to 100° C. and calcined followed by sintering to give a ceramic body containing zinc in the form of a solid solution.

In conducting the sintering treatment of the zinc-containing tricalcium phosphate powder, it is advantageous that the powder is blended with a suitable binder and is compression-molded into a powder compact or green body which is subjected to sintering. Polyvinyl alcohols are used as the binder in most cases, though not particularly limitative thereto provided that a green body of a substantial form can be retained therewith.

The process of sintering of the green body is performed at a temperature in the range from 900 to 1200° C. or, preferably, from 1050 to 1200° C.

When the content of zinc in the ceramic material is too low, i.e. less than 0.0126% by weight, sustained release of zinc from the ceramic material cannot be obtained while, when the content of zinc in the ceramic material is too high, toxicity of zinc against living body would possibly be exhibited due to an excessively large amount of zinc released in the living body.

The above mentioned upper limit of the content of zinc in the ceramic material is selected as a 100 times amount of the zinc content in an average human bone. Namely, it is reported that human bones usually contain from 0.0126 to 0.0200% by weight of zinc. In order that a pharmaceutical effects can be expected by the zinc ingredient contained in the ceramic material as a prosthetic substitute having sustained releasability of zinc, the zinc concentration in the ceramic material should be substantially larger than the zinc concentration in the natural bone but must not be too high.

Besides the above described process of sintering of a green body prepared directly from a tricalcium phosphate powder obtained by the liquid-phase reaction method and containing from 0.0126 to 1.26% by weight of zinc, the ceramic material of the invention can be prepared alternatively by preparing a green body from a powder mixture consisting of a tricalcium phosphate powder containing from 0.0150 to 8.00% by weight of zinc and a hydroxyapatite powder and/or a tricalcium phosphate powder free from zinc in such a proportion that the content of zinc in the resultant powder blend is in the range from 0.0126 to 1.26% by weight or, preferably, from 0.06 to 0.70% by weight. The mixing ratio of the zinc-doped tricalcium phosphate powder and a hydroxyapatite powder and/or undoped tricalcium phosphate powder is such that the molar ratio of (Zn+Ca)/P of the mixture is in the range from 1.55 to 1.65 which corresponds to the molar ratio of (Zn+Ca)/P of the mineral phase in human hard-tissues. Thus-prepared green body is sintered.

To explain this process in more detail, a tricalcium phosphate powder containing from 0.0150 to 8.00% by weight of zinc in the form of a solid solution is first prepared in the same precipitation method as described above followed by disintegration into fine particles. The thus-obtained zinc-doped tricalcium phosphate powder is then admixed and diluted with a powder of hydroxyapatite and/or a powder of undoped tricalcium phosphate in such a way that the (Zn+Ca)/P molar ratio of the mixed powder is in the range from 1.55 to 1.65 and that the content of zinc in the resultant powder blend is in the range from 0.0126 to 1.26% by weight or, preferably from 0.06 to 0.70% by weight. The powder blend is further admixed with a binder and compression-molded into a green body which is subjected to a sintering treatment under the same conditions as described above. Needless to say, the content of zinc in the zinc-doped tricalcium phosphate powder is substantially higher than the content of zinc in the finally obtained composite ceramic material as the target product prepared by dilution with a powder of hydroxyapatite and/or a powder of undoped tricalcium phosphate.

The reason for the lower limit of 0.0150% by weight in the content of zinc in the zinc-doped tricalcium phosphate powder before dilution is that, when the content of zinc is too low, the content is so close to the lower limit of 0.0126% by weight in the sintered composite ceramic material that the dilution method with hydroxyapatite and/or undoped tricalcium phosphate as the diluent no longer has significance. On the other hand, the upper limit of 8.00% by weight is the critical concentration of zinc for the formation of a solid solution, above which the excessive amount of zinc is liable to the formation of $CaZn_2(PO_4)_2$ and a glassy phase which may be more toxic against living body than the zinc in the form of a solid solution. The range of (Zn+Ca)/P molar ratio of the composite ceramic body corresponds to that of the human hard tissue, within which the composite ceramic body may be more biocompatible than the zinc-doped tricalcium phosphate ceramic bodies with a (Zn+Ca)/P molar ratio of 1.50. As is readily understood by considering the ionic radius of zinc, like magnesium and iron, in the range from 0.06 to 0.08 nm, zinc ions can easily form a solid solution in the host phase of the tricalcium phosphate when the content of zinc is within the above specified range.

In contrast thereto, hydroxyapatite hardly forms a solid solution with the metal ions including zinc having the above mentioned ionic radius. On the other hand, it is known that tricalcium phosphate, when dissolved in water or in a body fluid, is converted into hydroxyapatite which is thermodynamically more stable. When a zinc-doped tricalcium phosphate ceramic material or the above-mentioned composite ceramic material, which is prepared from a zinc-doped tricalcium phosphate in the form of a solid solution, is kept in a living body, accordingly, the zinc-doped tricalcium phosphate phase is gradually dissolved in the body fluid to produce ions of Ca, $PO_4$ and Zn, of which the ions of Ca and $PO_4$ ions alone can be converted into apatite to release the zinc ions only into the body fluid around the implanted ceramic material to exhibit some advantageous effects of promotion of osteogenesis, prevention of bone resorption and promotion of tissue restoration.

The ceramic body of the present invention capable of sustainedly releasing zinc in a living body is highly biocompatible as a ceramic material in itself because the ceramic material consists of the phase of tricalcium phosphate or of a combination of the phases of tricalcium phosphate and hydroxyapatite each having high biocompatibility and the content of zinc therein is limited not to exceed 100 times of the concentration of zinc in bone. When the ceramic body is kept within a living body, the ceramic material containing zinc in the form of a solid solution is gradually dissolved in the body fluid forming hydroxyapatite from the ions of Ca and $PO_4$ and releasing zinc ions into the surrounding tissues to exhibit various advantageous effects mentioned above.

In the following, the zinc-doped ceramic material of the present invention and the method for the preparation thereof are described in more detail by way of Examples.

The ceramic materials prepared in the following Examples were subjected to the phase analysis by the powder X-ray diffraction method and to the zinc-leaching test by dipping the ceramic body in an acetate buffer solution or in a cell culture medium. Further, in order to demonstrate the utilizability of the inventive ceramic materials for prosthesis, an in vitro toxicity test was undertaken by culturing osteo-blastic cells on the ceramic body and an in vivo osteogenetic test was undertaken by implanting the ceramic body into the femur of rabbits.

EXAMPLE 1

Calcium ethoxide, a 85% aqueous solution of phosphoric acid and zinc acetate were mixed together in ethyl alcohol in such a proportion that the molar ratio of (Ca+Zn)/P was 1.50 and the molar ratio of Zn/(Ca+Zn) was varied in the range up to 0.20 including a formulation with omission of zinc acetate to effect precipitation of zinc-doped tricalcium phosphate, which was collected by filtration, washed with ethyl alcohol, dried and calcined at 850° C. The calcined material was disintegrated into a fine powder, which was admixed with 3% by weight of a polyvinyl alcohol and the blend was compression-molded into a powder compact which was subjected to sintering at a temperature of 1100° C. for 5 hours to give a ceramic body. The formulations of the starting materials corresponded to up to 12% by weight of the content of zinc in the ceramic body.

Figure 1:
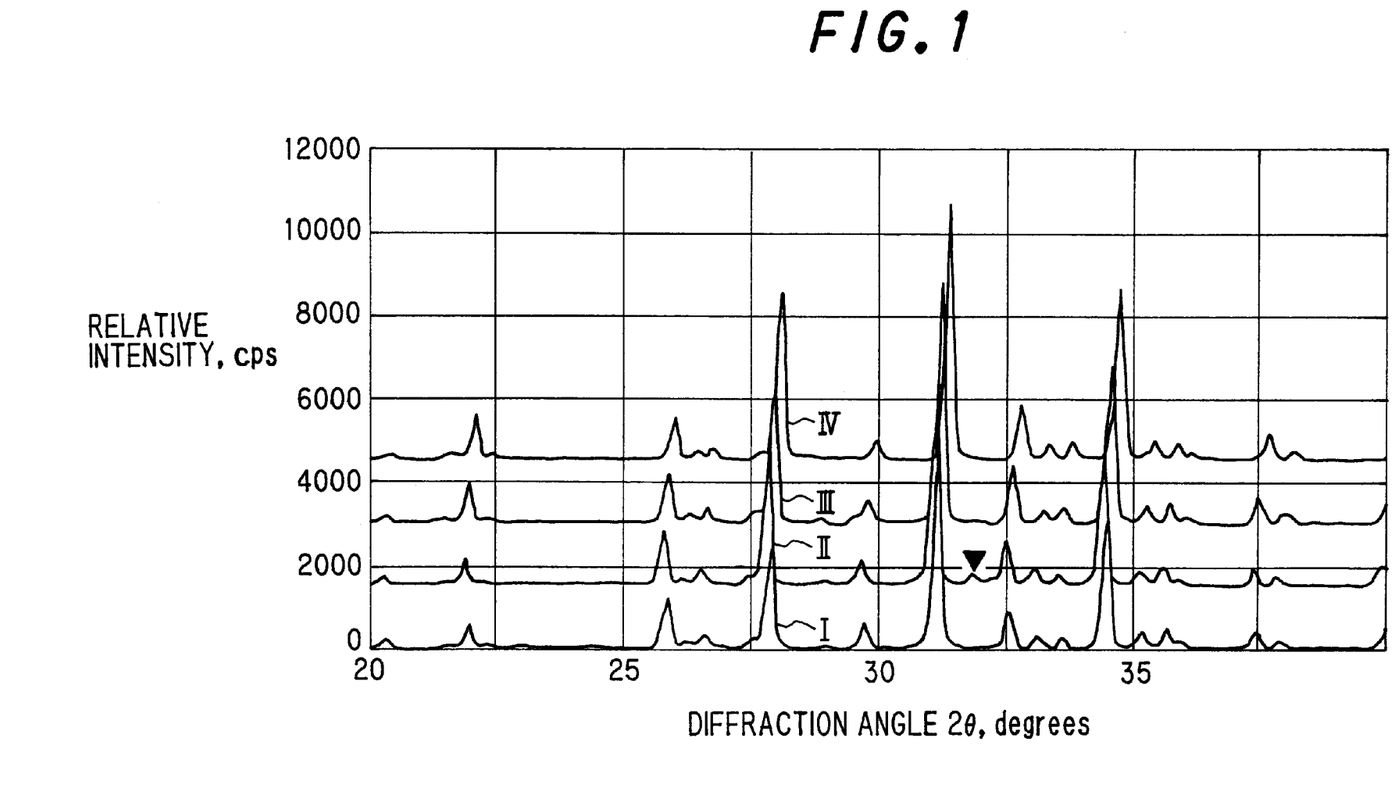
FIG. 1 shows powder X-ray diffraction patterns of tricalcium phosphate-based ceramic materials doped with varied amounts of zinc in the form of a solid solution.

The thus-obtained ceramic bodies with varied contents of zinc were each subjected to the phase analysis by the powder X-ray diffractometry using the CuKa line to find that the ceramic body consisted of the phase of β-tricalcium phosphate known to have high biocompatibility or a combination of the phase of β-tricalcium phosphate and a minor phase of hydroxyapatite when the content of zinc in the ceramic body did not exceed 8.00% by weight to indicate that zinc was contained in the tricalcium phosphate in the form of a solid solution. When the content of zinc exceeded 8.00% by weight, on the other hand, the X-ray diffraction pattern indicated presence of $CaZn_2(PO_4)_2$ and a glassy phase as impurities. The X-ray diffraction patterns are shown in FIG. 1, in which the pattern I is for a powder of tricalcium phosphate prepared without addition of zinc acetate and the patterns II, III and IV are for those containing 0.63% by weight, 3.12% by weight and 7.99% by weight, respectively, of zinc and the peaks indicated by the mark ▼ on the pattern II are assignable to hydroxyapatite.

The above described results of the X-ray diffractometry lead to a conclusion that zinc can be contained in tricalcium phosphate in the form of a solid solution up to a content of 8.00% by weight and the ceramic bodies containing 0.0126 to 1.26% by weight of zinc consist of a combination of tricalcium phosphate and a minor amount of hydroxyapatite having high biocompatibility.

EXAMPLE 2

Figure 2:
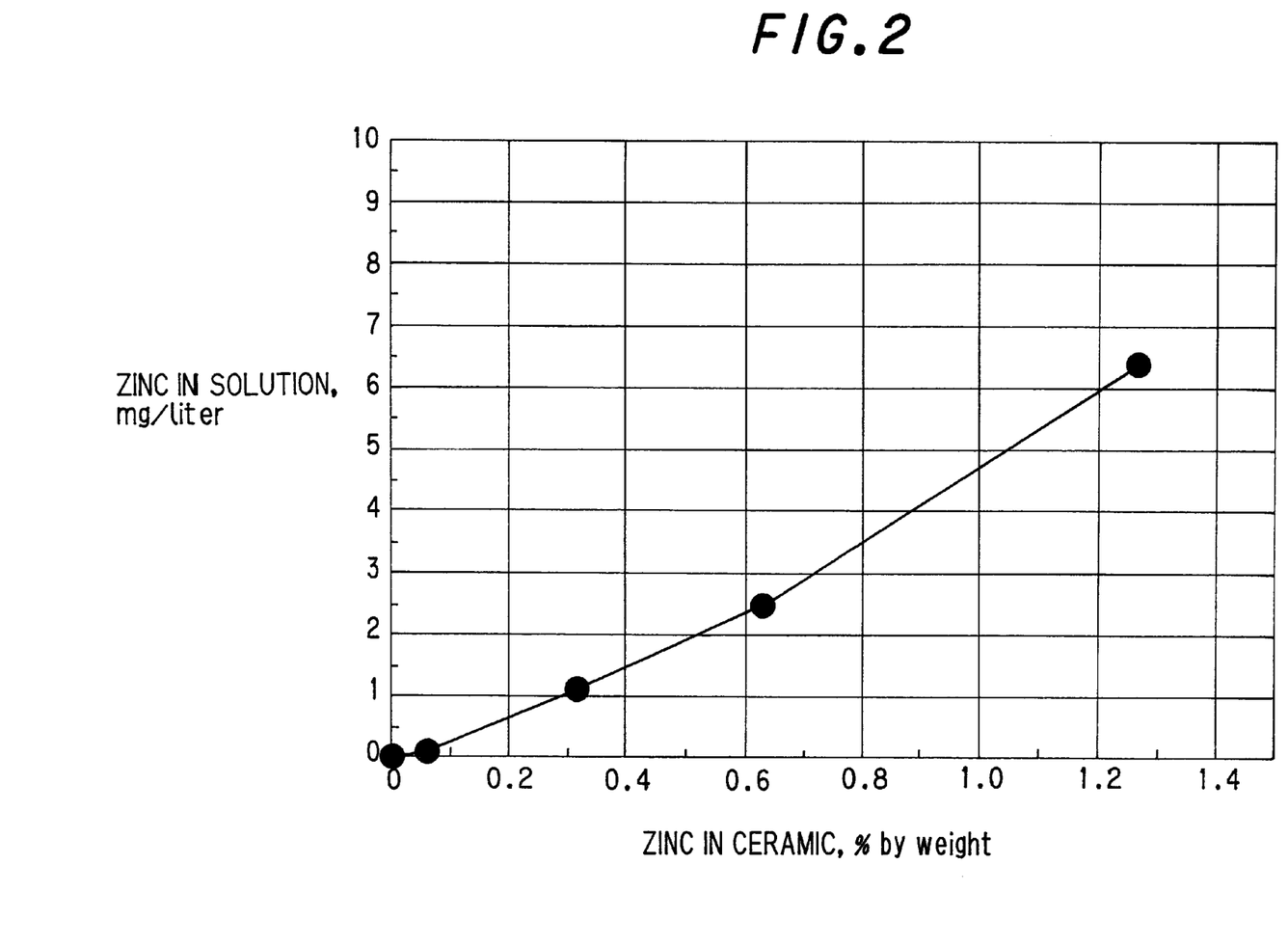
FIG. 2 is a graph showing the amount of zinc leached out into an acetate buffer solution from tricalcium phosphate-based ceramic materials doped with varied amounts of zinc in the form of a solid solution as a function of the content of zinc in the ceramic materials.

A tricalcium phosphate-based ceramic disk having a diameter of 13 mm and a thickness of 1 mm and containing zinc in a varied content of up to 1.26% by weight and prepared in the same manner as in Example 1 was kept immersed in 50 ml of an acetic acid-sodium acetate buffer solution having a pH of 5.0 at 37° C. for 60 days. Thereafter, the buffer solution was subjected to the ICP analysis for the concentration of zinc to give the results shown by the graph of FIG. 2 which gives the concentration of zinc in the solution as a function of the content of zinc in the ceramic body.

EXAMPLE 3

A cylindrical tricalcium phosphate-based ceramic body having a diameter of 2.5 mm and a length of 10 mm and containing a varied amount of zinc up to 0.316% by weight in the form of a solid solution was prepared in substantially the same manner as in Example 1. The thus-prepared ceramic body was implanted into the femur of a rabbit under anesthesia. For the purpose of control, a tricalcium phosphate-based ceramic body having the same dimensions was prepared in the same manner as above excepting for the omission of the zinc dopant and used in the in vivo test. The zinc-doped and undoped ceramic bodies were implanted into the femur of different rabbits.

Figure 3:
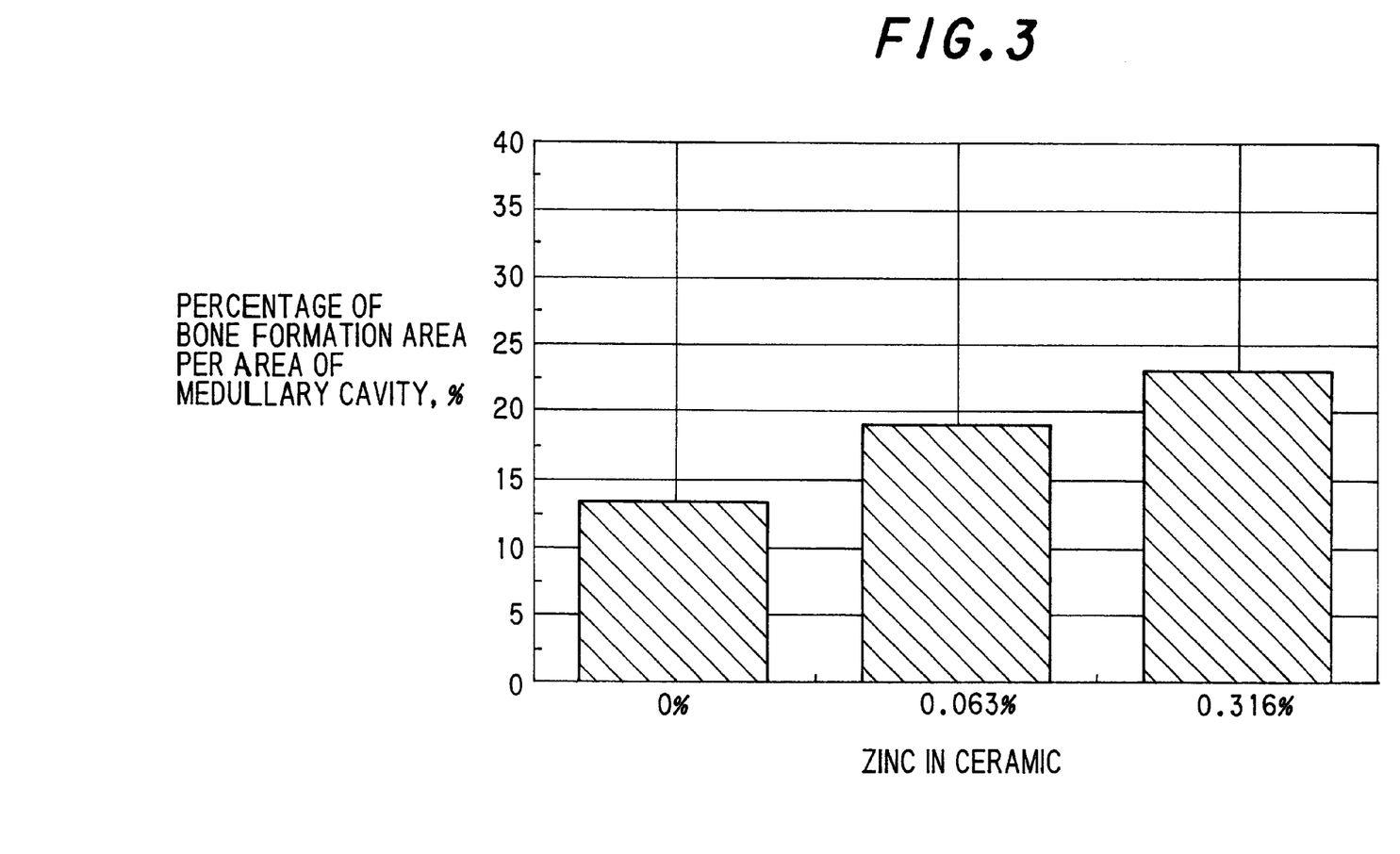
FIG. 3 is a bar chart showing the amount of newly formed bone around the ceramic bodies of zinc-doped tricalcium phosphate with three different zinc contents implanted in the femur of rabbits. The amount of newly formed bone is expressed as the area of newly formed bone per the area of the medullary cavity.

After raising for one month in a usual manner, the rabbit was killed and the femur taken out from the rabbit body was sliced in parallel to the axis of the cylindrical ceramic body implanted therein to give thin sections which were dyed and subjected to a microscopic examination for the amount of bone tissue around the ceramic body. The microscopic images of the thin sections were computer-processed to conduct image analysis to determine the area of the bone tissue newly formed around the ceramic body. FIG. 3 is a bar chart showing the amount of the newly formed bone around the ceramic bodies of zinc-doped tricalcium phosphate with three different zinc contents implanted in the femur of rabbits. The amount of the newly formed bone is expressed as the area of the newly formed bone per the area of the medullary cavity. The amount of the newly formed bone around the ceramic body was increased with an increase in the content of zinc in the zinc-doped ceramic body. The amount of the newly formed bone, however, was statistically insignificant. No fibrous connective tissue was detected between the ceramic body and the femur bone indicating high biocompatibility of the ceramic body of zinc-doped tricalcium phosphate.

EXAMPLE 4

Figure 4:
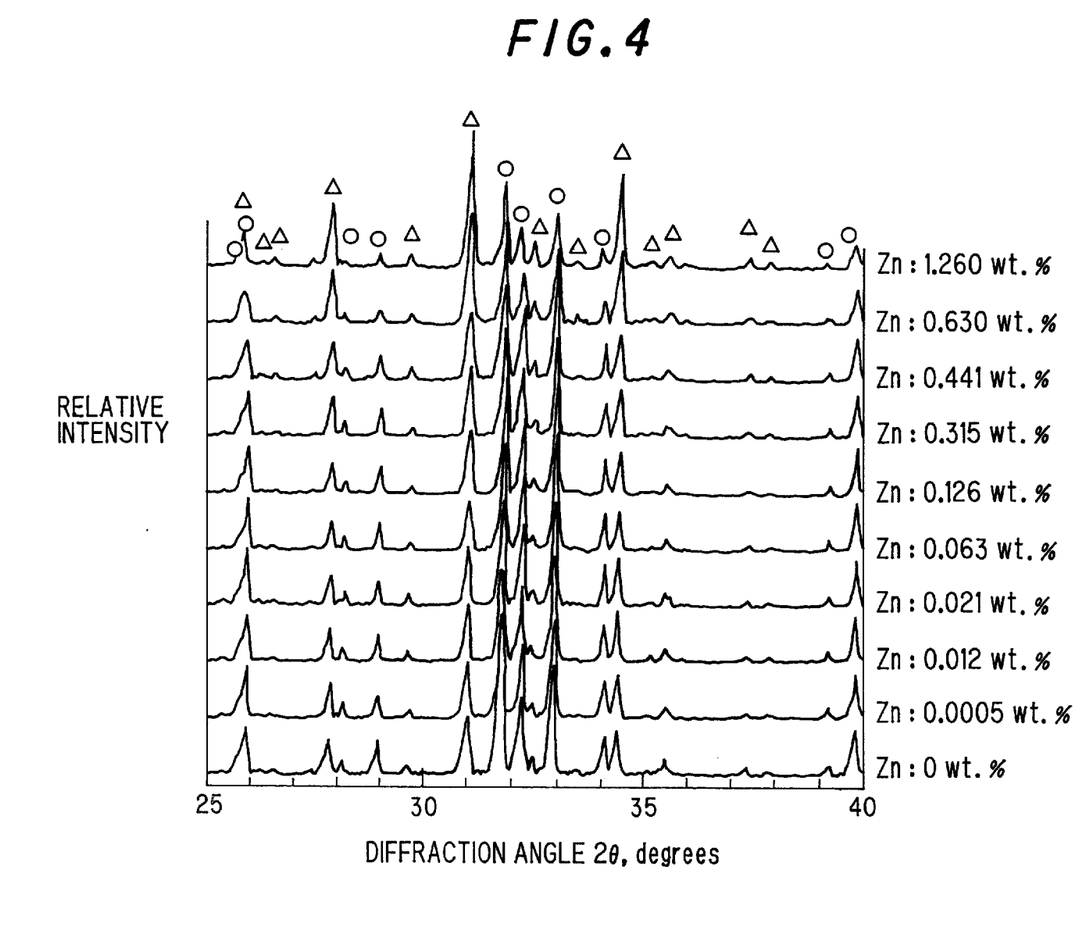
FIG. 4 shows powder X-ray diffraction patterns of tricalcium-phosphate-based composite ceramic materials doped with varied amounts of zinc in the form of a solid solution.

A powder of tricalcium phosphate containing 7.99% by weight of zinc in the form of a solid solution was prepared by blending an aqueous suspension or aqueous solution of 1.620 moles of calcium hydroxide, 1.20 moles of phosphoric acid and 0.180 mole of zinc nitrate to form precipitates of phosphate which were collected by filtration, washed with water, dried, calcined at 850° C. and disintegrated into a fine powder. The thus-obtained zinc-containing tricalcium phosphate powder was uniformly blended with varied amounts of powders of undoped tricalcium phosphate and hydroxyapatite in such a proportion as to give a (Ca+Zn)/P molar ratio of 1.60 together with polyvinyl alcohol as a binder in an amount of 3% by weight based on the total amount of the powders. The powder blend was compression-molded into a green body which was subjected to sintering at 1100° C. for 1 hour to give a composite ceramic body containing a varied content of zinc up to 1.26% by weight. The thus-obtained composite ceramic bodies were subjected to the powder X-ray diffraction analysis to obtain the diffraction patterns shown in FIG. 4 including the pattern for a composite of tricalcium phosphate and hydroxy-apatite without zinc, in which the peaks indicated by the mark ○ were assignable to hydroxyapatite and the peaks indicated by the mark Δ were assignable to β-tricalcium phosphate. It was understood from these diffraction patterns that each of the composite ceramic bodies containing from 0.0126% by weight to 1.26% by weight of zinc consisted of the phases of β-tricalcium phosphate and hydroxyapatite alone.

EXAMPLE 5

Figure 5:
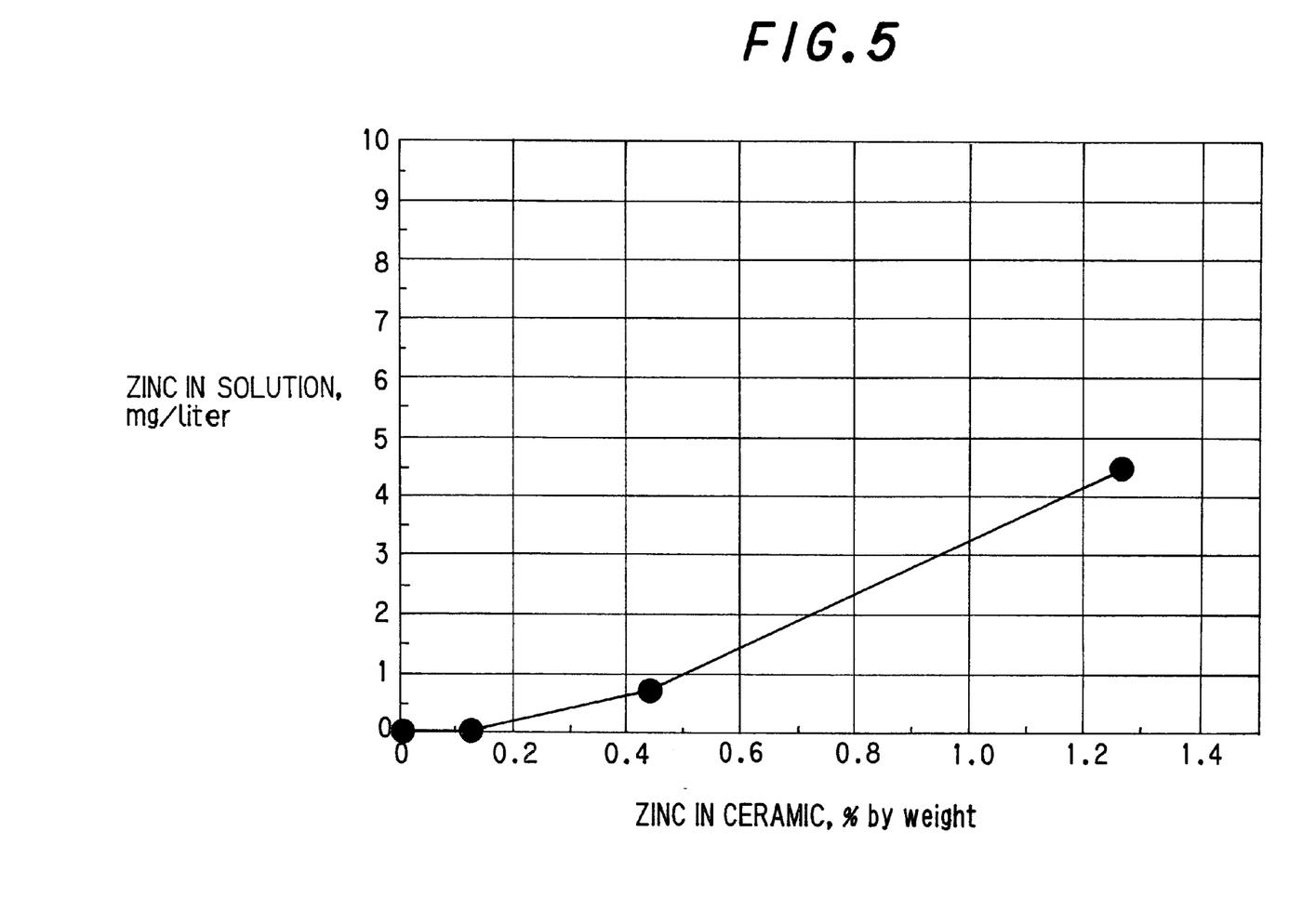
FIG. 5 is a graph showing the amount of zinc leached out into an acetate buffer solution from the tricalcium-phosphate-based composite ceramic materials doped with varied amounts of zinc in the form of a solid solution as a function of the content of zinc in the ceramic materials.
Figure 6:
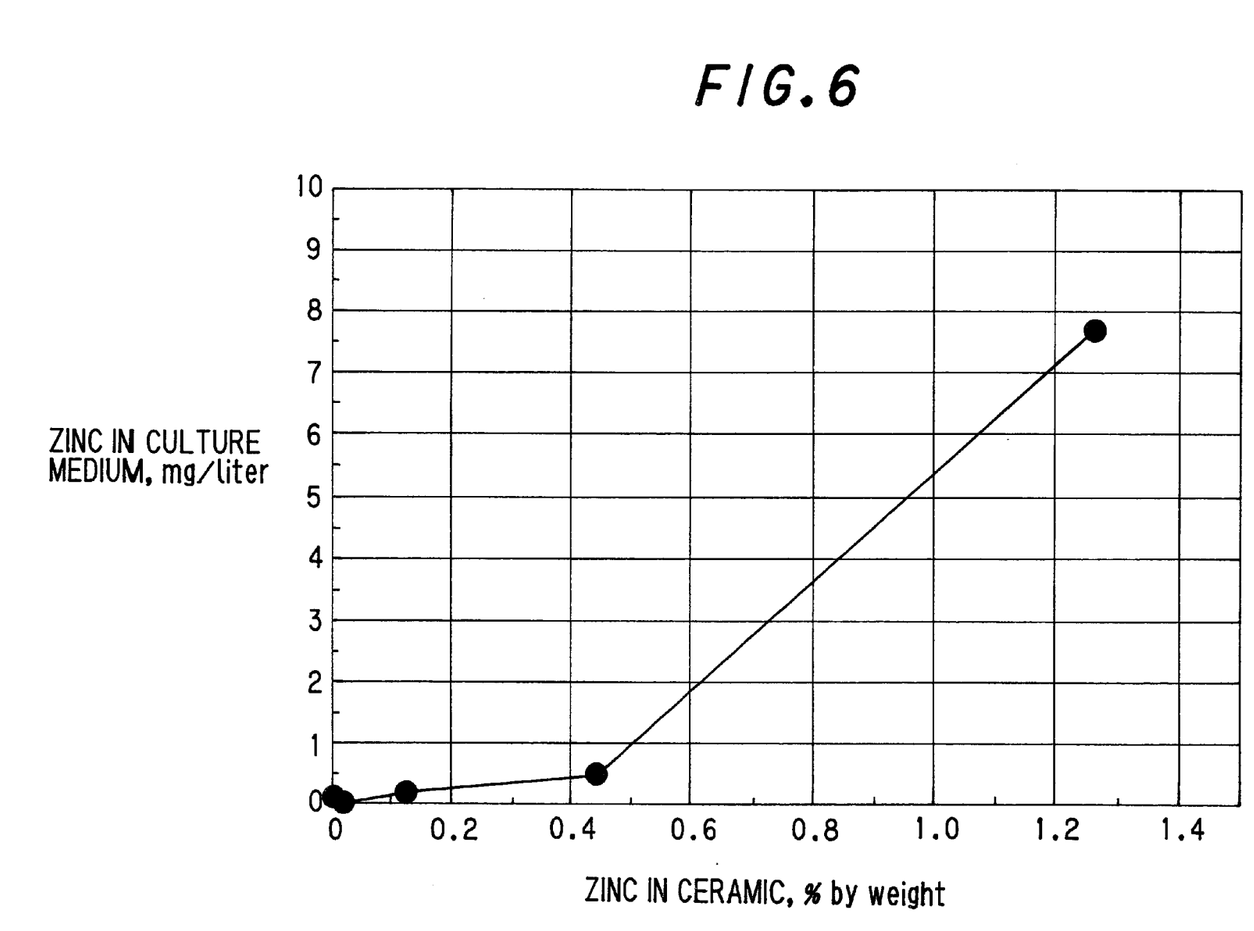
FIG. 6 is a graph showing the amount of zinc leached out into a cell culture medium from the tricalcium-phosphate-based composite ceramic materials doped with varied amounts of zinc in the form of a solid solution as a function of the content of zinc in the ceramic materials.

Zinc-doped-tricalcium-phosphate-based composite ceramic disks having a diameter of 13 mm and a thickness of 1 mm and containing zinc in a varied amount up to 1.26% by weight were subjected to the zinc-leaching test in an acetate buffer solution under the same conditions as in Example 2 described above to give the results shown in FIG. 5. For better simulation to the in vivo conditions, separately, five of the same composite ceramic disks were immersed and kept standing in 5 ml of a cell culture medium at 37° C. for 7 days under an atmosphere containing 5% by volume of carbon dioxide. Thereafter, the cell culture medium was subjected to the ICP analysis for the concentration of zinc to give the results shown in FIG. 6 as a function of the content of zinc in the composite ceramic body.

EXAMPLE 6

Tricalcium-phosphate-based composite ceramic disks of 13 mm diameter and 1 mm thickness undoped or doped with zinc were each taken in a dish for cell culture having a diameter of 16 mm into which 500 of osteoblastic MC3T3-E1 cells originating from mouse and 1 ml of a cell culture medium were introduced. The cell culture was conducted at 37° C. for 4 days on the composite ceramic disk. The osteoblastic MC3T3-E1 cell here implied is a precursor cell of the osteoblast which differentiates into the osteoblast. After completion of cell culture, the cells on the composite ceramic disk were fixed with glutaraldehyde and stained to be counted under a microscope to record the number of cells on the ceramic disk, from which calculation was made for the relative growth rate, which was the ratio of the number of the cells on the zinc-doped composite ceramic disk to the number of the cells on the undoped composite ceramic disk to give the results shown by the graph of FIG. 7 giving the values of the relative growth rate as a function of the content of zinc in the composite ceramic disks in a semilogarithmic scale.

Figure 7:
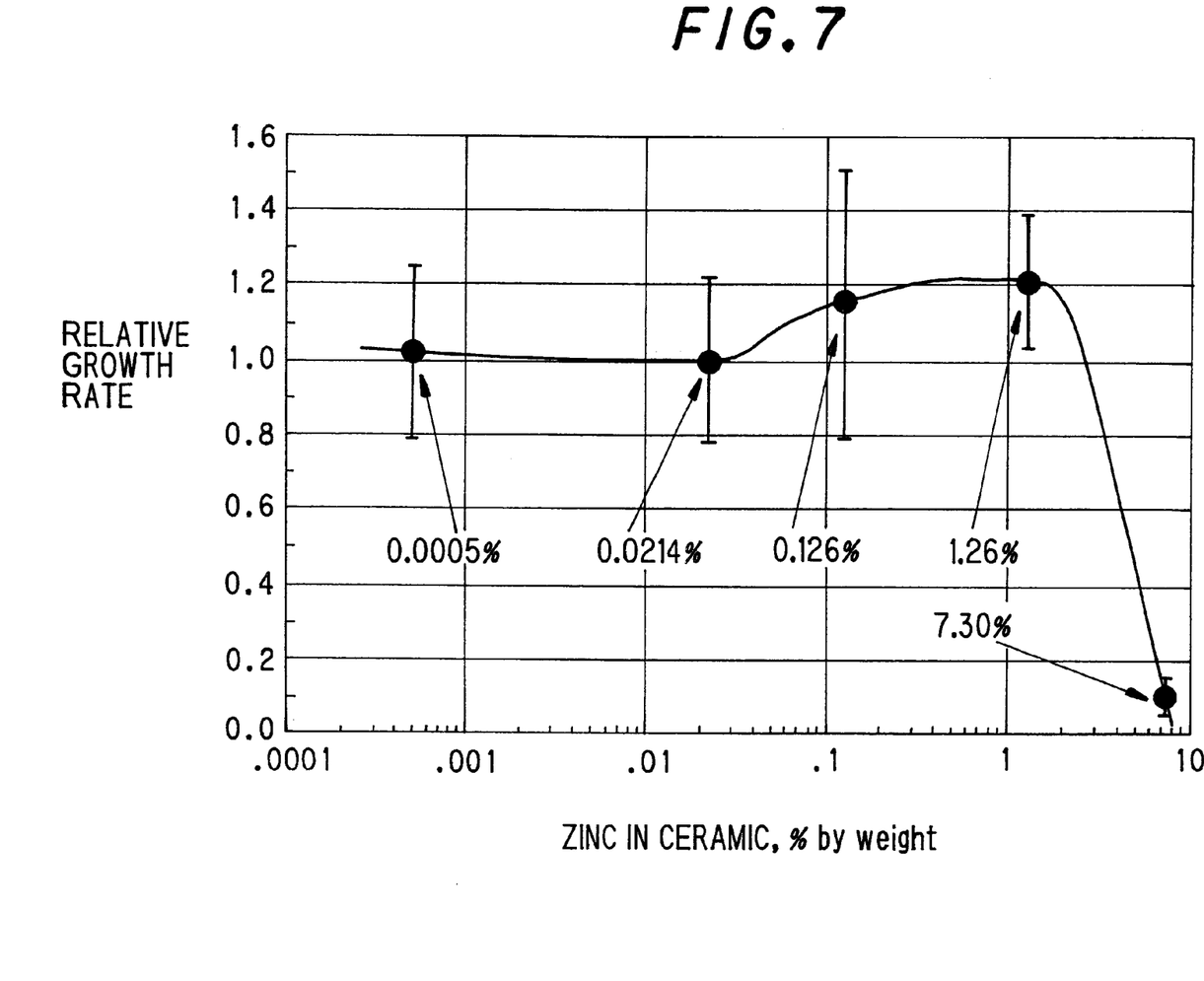
FIG. 7 is a graph showing the relative growth rate of MC3T3-E1 osteogenic cells on the tricalcium-phosphate-based composite ceramic body doped with varied amounts of zinc as a function of the content of zinc in the ceramic materials.

It was understood from FIG. 7 that an osteogenesis-promoting effect could be obtained when the content of zinc in the composite ceramic disk was in the range from 0.0126 to 1.26% by weight while the relative growth rate was rapidly decreased by increasing the content of zinc in the ceramic disk over 1.26% by weight indicating appearance of toxicity by zinc.

EXAMPLE 7

Figure 8:
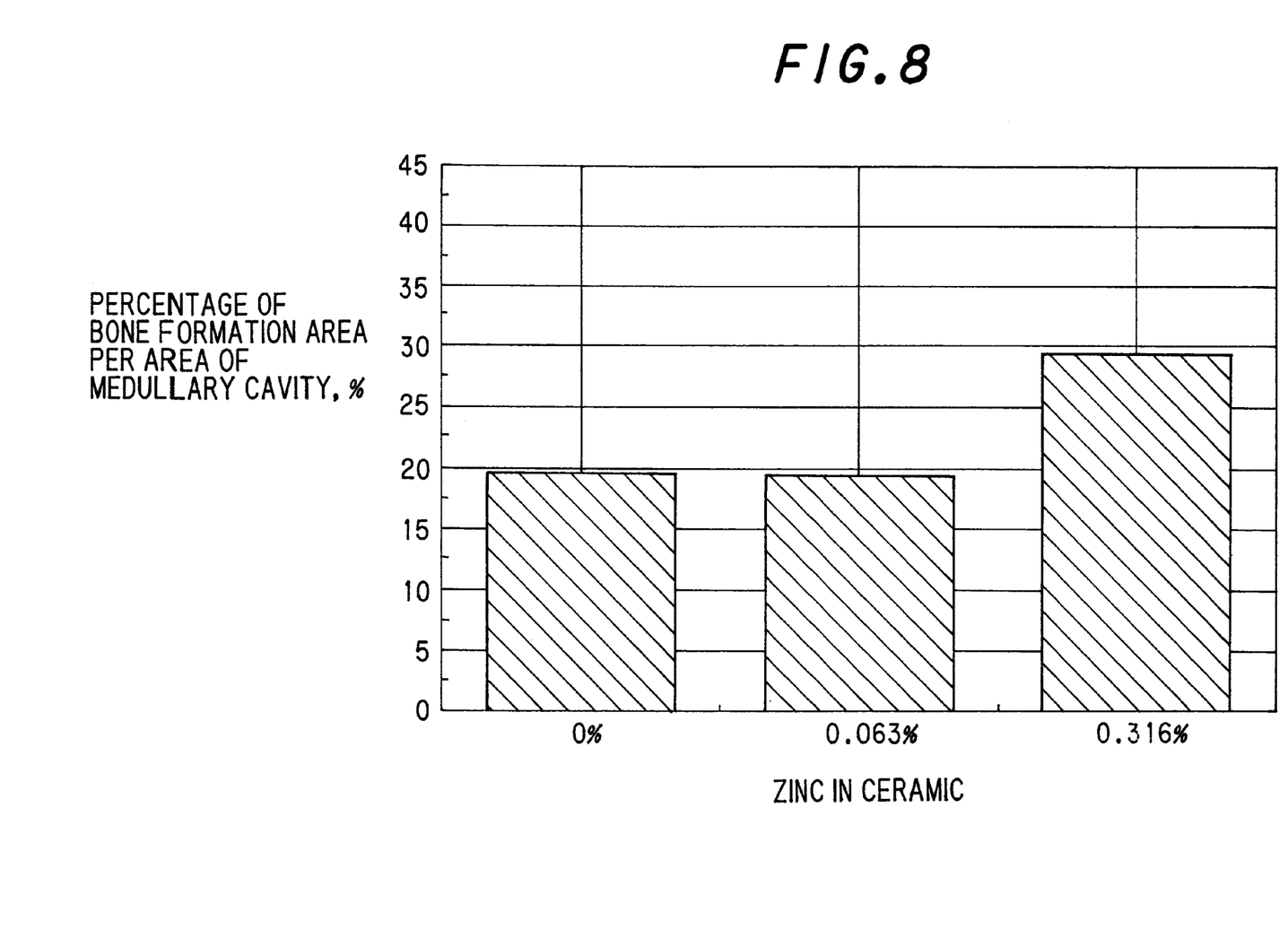
FIG. 8 is a bar chart showing the amount of newly formed bone around the composite ceramic body containing zinc-doped tricalcium phosphate with three different zinc contents implanted in the femur of rabbits. The amount of newly formed bone is expressed as the area of newly formed bone per the area of the medullary cavity. The zinc contents are expressed as the weight of zinc with respect to the weight of the composite ceramic.

An in vivo test for bone formation using rabbits as the test animal was undertaken in the same manner as in Example 3 excepting for the use of composite ceramic bodies containing up to 0.316% by weight of zinc. A control test was undertaken by using composite ceramic bodies without containing zinc. FIG. 8 is a bar chart showing the amount of the newly formed bone around the composite ceramic bodies based on the zinc-doped tricalcium phosphate in three different zinc contents implanted in the femur of rabbits. The amount of newly formed bone is expressed as the area of the newly formed bone per the area of the medullary cavity. FIG. 8 indicates the osteogenesis-promoting effect of the zinc-doped composite ceramic body. For example, the osteogenesis-promoting effect of the composite ceramic body containing 0.316% by weight of zinc was statistically significant at a significance level of 5.5% with the number of samples n=6 (p=0.0509). No fibrous connective tissue was detected between the surface of the composite ceramic body and the newly formed bone tissue.

EXAMPLE 8

An in vivo test for bone formation using rabbits as the test animal was undertaken in the same manner as in Example 3 by implanting the tricalcium phosphate-based composite ceramic bodies containing 0.316% by weight of zinc into the femur of the rabbits for a varied implantation period up to 12 weeks. A control test was concurrently undertaken by using similar ceramic bodies without containing zinc. The zinc-doped and undoped ceramic bodies were implanted into each femur of the same rabbit.

Figure 9:
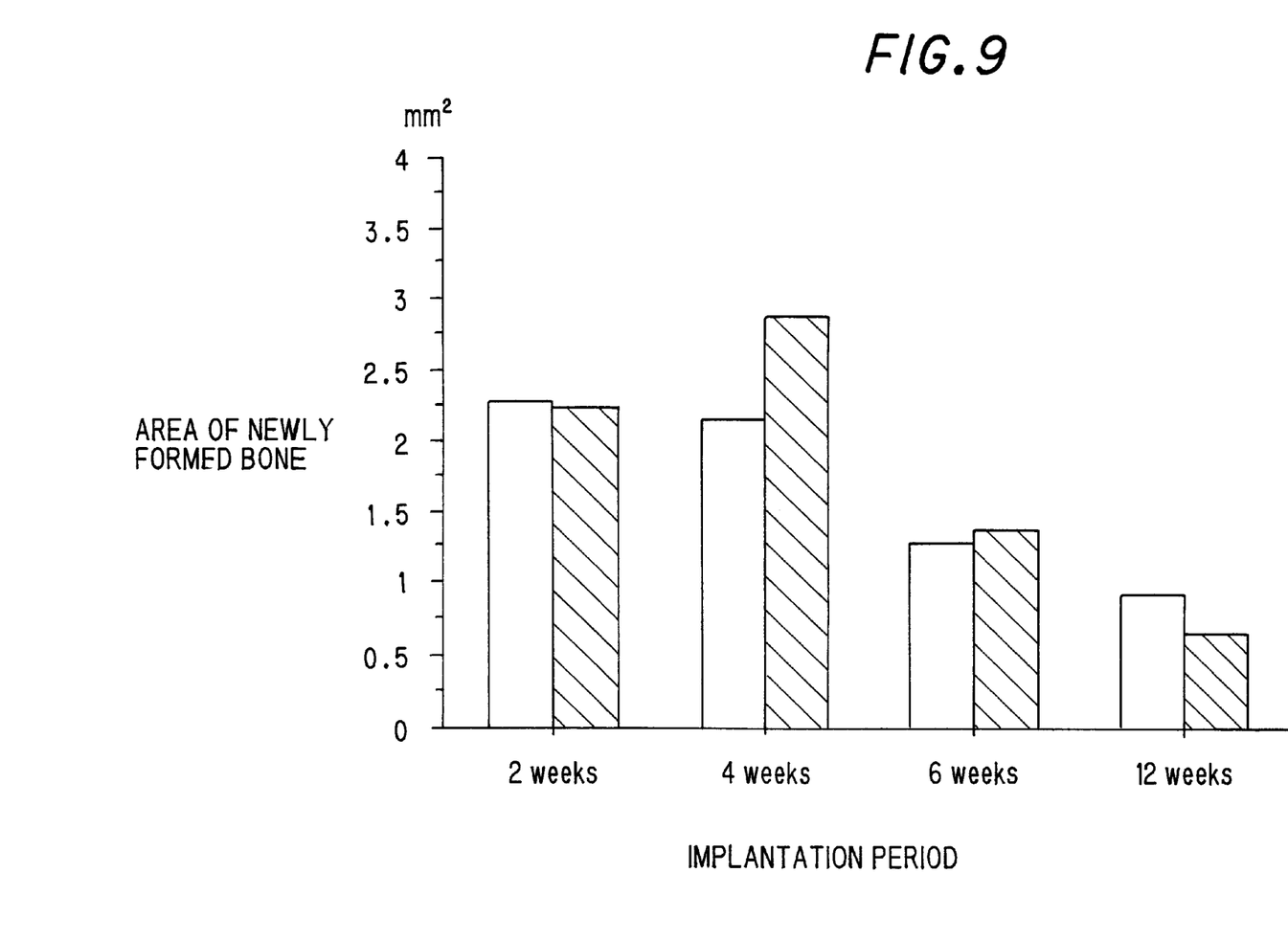
FIG. 9 is a bar chart showing the amount of the newly formed bone around the composite ceramic body consisting of zinc-doped tricalcium phosphate with a zinc content of 0.316% by weight (hatched bars) and without zinc for control (open bars). The content of zinc is expressed as the weight of zinc with respect to the weight of the composite ceramic. The amount of the newly formed bone is expressed as the area of the newly formed bone.

FIG. 9 is a bar chart showing the amount of the newly formed bone expressed as the area of the newly formed bone around the zinc-doped composite ceramic body (hatched bars) and undoped composite ceramic body (open bars). FIG. 9 indicates that the zinc-doped composite ceramic body exhibits an osteogenesis-promoting effect. Namely, the osteogenesis-promoting effect of the composite ceramic body containing 0.316% by weight of zinc was statistically significant at a significance level of 5% with the number of samples n=6 (p=0.0429) after 4 weeks of the implantation period. No fibrous connective tissue was detected between the surface of the composite ceramic body and the newly formed bone tissue.

What is claimed is:

1. A sintered composite ceramic body consisting of hydroxy-apatite and tricalcium phosphate containing zinc in the form of a solid solution, in which the molar ratio of (Zn+Ca)/P is in the range from 1.55 to 1.65 and the content of zinc is in the range from 0.0126% to 1.26% by weight based on the ceramic body.

2. The sintered ceramic body as claimed in claim 1 in which the content of zinc is in the range from 0.06% to 0.70% by weight based on the ceramic body.

3. A method for the preparation of a sintered composite ceramic body as defined in claim 2 which comprises the steps of:
   (a) preparing a powder of tricalcium phosphate containing from 0.0150% to 8.00% by weight of zinc in the form of a solid solution;
   (b) blending the zinc-containing tricalcium phosphate powder prepared in step (a) with an adjuvant powder containing hydroxyapatite and optionary tricalcium phosphate free from zinc to give a powder blend in such a blending proportion that the content of zinc calculated as the zinc element in the powder blend is in the range from 0.0126% to 1.26% by weight and the molar ratio of (Ca+Zn)/P is in the range from 1.55 to 1.65;
   (c) shaping the powder blend prepared in step (b) into a green body; and
   (d) sintering the green body by heating at a temperature in the range from 900° to 1200° C.

4. A method of providing a prosthesis for a hard living body tissue with a substitute material which comprises the step of: implanting, into the living body, a substitute material which is the sintered ceramic body as defined in claim 1.

* * * * *